United States Patent
Kawazoe et al.

(10) Patent No.: US 8,117,892 B2
(45) Date of Patent: Feb. 21, 2012

(54) HARDNESS TESTING INSTRUMENT AND CALIBRATION METHOD THEREOF

(75) Inventors: Masaru Kawazoe, Kawasaki (JP); Masato Suzuki, Yokohama (JP)

(73) Assignee: Mitutoyo Corporation, Kawasaki (JP)

(*) Notice: Subject to any disclaimer, the term of this patent is extended or adjusted under 35 U.S.C. 154(b) by 483 days.

(21) Appl. No.: 12/292,884

(22) Filed: Nov. 28, 2008

(65) Prior Publication Data
US 2009/0145196 A1 Jun. 11, 2009

(30) Foreign Application Priority Data

Dec. 7, 2007 (JP) ................. 2007-317404

(51) Int. Cl.
- G01B 21/30 (2006.01)
- G01N 3/62 (2006.01)
- G01N 3/48 (2006.01)
- G01N 11/00 (2006.01)
- G01C 17/38 (2006.01)

(52) U.S. Cl. ............... 73/1.89; 73/81; 73/823; 702/94
(58) Field of Classification Search ............. 73/1.89, 73/81–82, 1.15; 702/43
See application file for complete search history.

(56) References Cited

U.S. PATENT DOCUMENTS

| | | | |
|---|---|---|---|
| 4,667,509 A * | 5/1987 | Tobolski et al. | 73/83 |
| 5,999,887 A * | 12/1999 | Giannakopoulos et al. | 702/33 |
| 7,568,381 B2 * | 8/2009 | Smith et al. | 73/81 |

FOREIGN PATENT DOCUMENTS

| | | | |
|---|---|---|---|
| JP | 200191434 A | * | 4/2001 |
| JP | 3170256 B | | 5/2001 |

OTHER PUBLICATIONS

Machine Translation of JP 2001-91434, Hardness Testing Machine and Force Testing Mehtod, Date: Jun. 4, 2001.*
Machine Translation of JP 2001-91434, Hardness Testing Machine and Force Testing Method, Date: Jun. 4, 2001.*

* cited by examiner

Primary Examiner — Lisa Caputo
Assistant Examiner — Roger Hernandez-Prewitt
(74) Attorney, Agent, or Firm — Oliff & Berridge, PLC

(57) ABSTRACT

Disclosed is a hardness testing instrument which measures a hardness of a specimen, the hardness testing instrument including: a load applying section with the indenter or a flat indenter mounted thereon; a driving section to move the load applying section; a specimen table on which an object to be pressed is placed; a specimen table height adjustment section to adjust a height position; an indentation depth amount storage section to measure the indentation depth amount when the indenter is pressed to a reference block and to store the amount; a deformation amount storage section to measure the deformation amount of a load measuring instrument when the flat indenter is pressed to the load measuring instrument and to store the amount; a height position obtaining section to obtain a height position of the specimen table; and a calibration section to calibrate the load.

4 Claims, 5 Drawing Sheets

HARDNESS TESTING INSTRUMENT AND CALIBRATION METHOD THEREOF

BACKGROUND OF THE INVENTION

1. Field of the Invention

The present invention relates to a hardness testing instrument and a calibration method for a hardness testing instrument.

2. Description of Related Art

There has been a hardness testing instrument well-known which measures a hardness of a specimen by forming an indentation with an indenter on a surface of the specimen (for example, Japanese Patent No. 3170256).

When force calibration is performed on the conventional hardness testing instrument, it is performed at one intermediate position of a mechanical stroke, and maintenance and management of quality is done by calibration at this one position.

In recent years, as improvement of traceability system is promoted, need is rising for performing calibration of force for three standards in the stroke of the hardness testing instrument, and quality management at a higher level is demanded.

However, there is a problem of when force calibration is performed on the conventional hardness testing instrument, in order to perform calibration of force (load) for the three standards, fine adjustment such as position adjustment of specimen table with respect to each standard needs to be performed, and complicated operation is necessary.

Specifically, in order to set a load cell for calibration at the target standard, after performing measurement of indentation depth using a reference block and measurement of distortion amount of the load cell, the moving amount of the specimen table needed to be determined by hand calculation. Also, measurement of the reference block needs to be performed each time due to individual difference according to model such as machine casing distortion of the hardness testing instrument.

In a conventional hardness testing instrument which performs a sequence of applying test force (load) at a set position of a specimen, after the test force is unloaded, the preliminary test force is still loaded, therefore the lifting and lowering device needs to be operated to lower the specimen table and the test force needs to be released. Therefore, when data is obtained a plurality of times, alignment of the height position of the load cell needs to be performed again after the release of the test force.

SUMMARY OF THE INVENTION

The present invention has been made in consideration of the above problems, and it is one of main objects to provide a hardness testing instrument and a calibration method of a hardness testing instrument with which calibration of load can be easily performed.

According to a first aspect of the present invention, there is provided a hardness testing instrument which measures a hardness of a specimen by pressing an indenter to a surface of the specimen, the hardness testing instrument comprising:

a load applying section with the indenter or a flat indenter mounted thereon;

a driving section to move the load applying section;

a specimen table on which an object to be pressed by the indenter or the flat indenter is placed;

a specimen table height adjustment section to adjust a height position of the specimen table;

an indentation depth amount storage section to move the load applying section from a reference position, to measure the indentation depth amount when the indenter is pressed with a predetermined load to a reference block having a predetermined hardness placed on the specimen table, and to store the indentation depth amount;

a deformation amount storage section to move the load applying section from the reference position, to measure the deformation amount of a load measuring instrument placed on the specimen table when the flat indenter is pressed with a predetermined load to the load measuring instrument, and to store the deformation amount;

a height position obtaining section to obtain a height position of the specimen table according to the hardness of the reference block based on calculating difference between the deformation amount stored in the deformation amount storage section and the indentation depth amount stored in the indentation depth amount storage section; and a calibration section to calibrate the load by comparing a value of the load measured by the load measuring instrument and a value of the predetermined load when the flat indenter is pressed with the predetermined load to the load measuring instrument placed on the specimen table adjusted by the specimen table height adjustment section to the height position of the specimen table obtained by the height position obtaining section.

According to a second aspect of the present invention, there is provided a calibration method for a hardness testing instrument to calibrate a hardness testing instrument comprising, a load applying section with the indenter or a flat indenter mounted thereon;

a driving section to move the load applying section;

a specimen table on which an object to be pressed by the indenter or the flat indenter is placed; and a specimen table height adjustment section to adjust a height position of the specimen table, the method comprising:

storing an indentation depth amount by placing the load applying section at a reference position by adjusting the height position of the specimen table so that the indenter is in contact with a plurality of reference blocks having different hardness placed on the specimen table, then moving the load applying section from the reference position to measure each indentation depth amount when the indenter is pressed with a predetermined load to each of the reference blocks, and storing the indentation depth amount in the storage section;

storing a deformation amount by placing the load applying section at a reference position by adjusting the height position of the specimen table so that the flat indenter is in contact with the load measuring instrument placed on the specimen table, then moving the load applying section from the reference position to measure the deformation amount of the load measuring instrument when the indenter is pressed with a predetermined load to the load measuring instrument, and storing the deformation amount in the storage section;

obtaining a height position of the specimen table according to the hardness corresponding to the plurality of reference blocks based on calculating difference between the deformation amount stored in the storage section and the indentation depth amount according to the hardness of the reference block stored in the storage section;

adjusting the specimen table height position by performing adjustment of the specimen table height to the height position of the specimen table obtained in the height position obtaining step when the flat indenter applies small enough force to the load measuring instrument placed on the specimen table; and calibrating the load by comparing a value of the load measured by the load measuring instrument and a value of the predetermined load when the flat indenter is pressed with the predetermined load to the load measuring instrument placed on the specimen table adjusted in the specimen table height position adjusting step.

BRIEF DESCRIPTION OF THE DRAWINGS

The above and other objects, advantages, and features of the present invention will become more fully understood from the detailed description given hereinbelow and the appended drawings which are given by way of illustration only, and thus are not intended as a definition of the limits of the present invention, and wherein.

DESCRIPTION OF THE PREFERRED EMBODIMENTS

A hardness testing instrument and a calibration method for the hardness testing instrument of an embodiment of the present invention will be described below with reference to the drawings.

Figure 1:
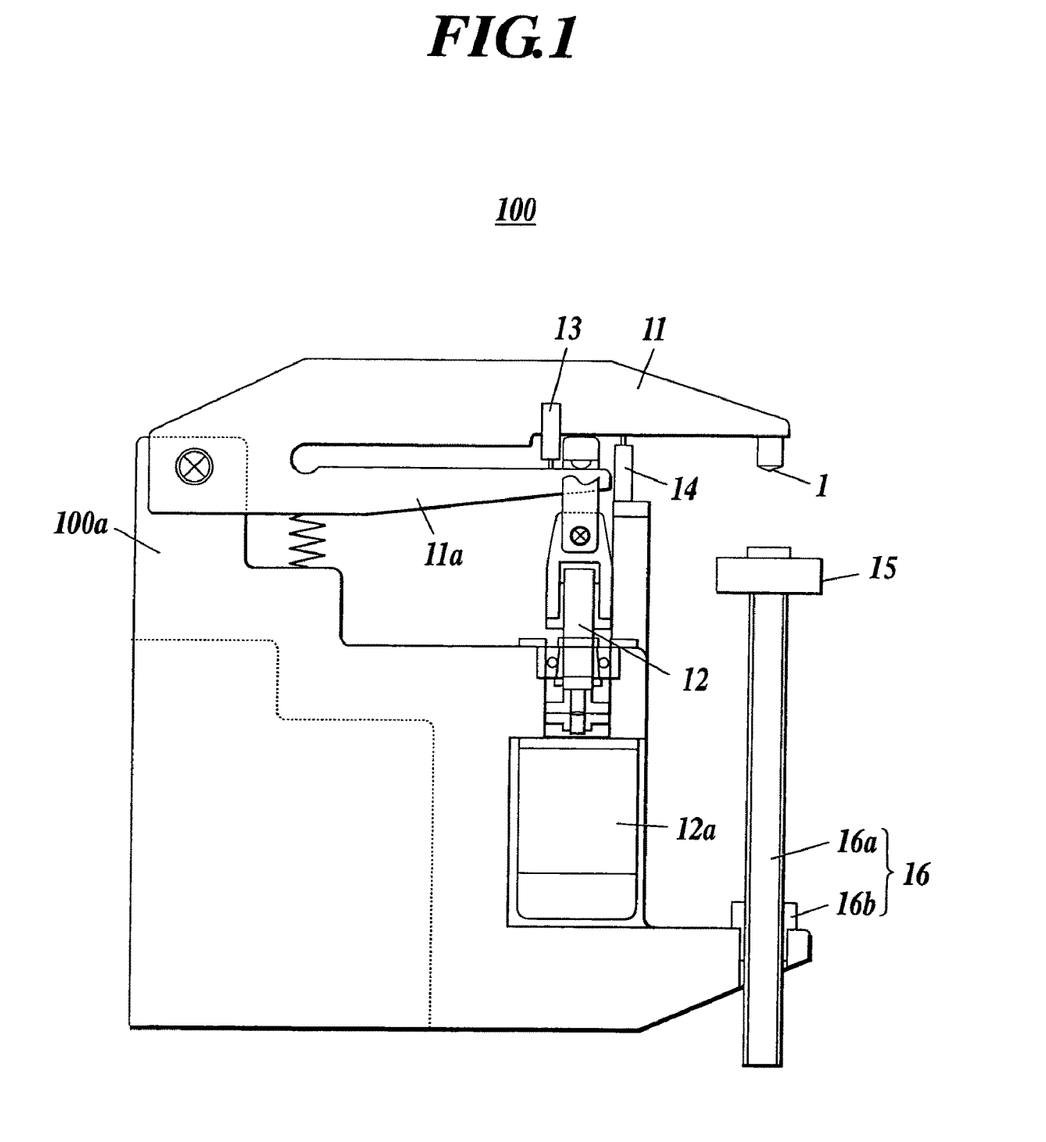
FIG. 1 is an external diagram showing a hardness testing instrument of the present embodiment from a lateral view.
Figure 2:
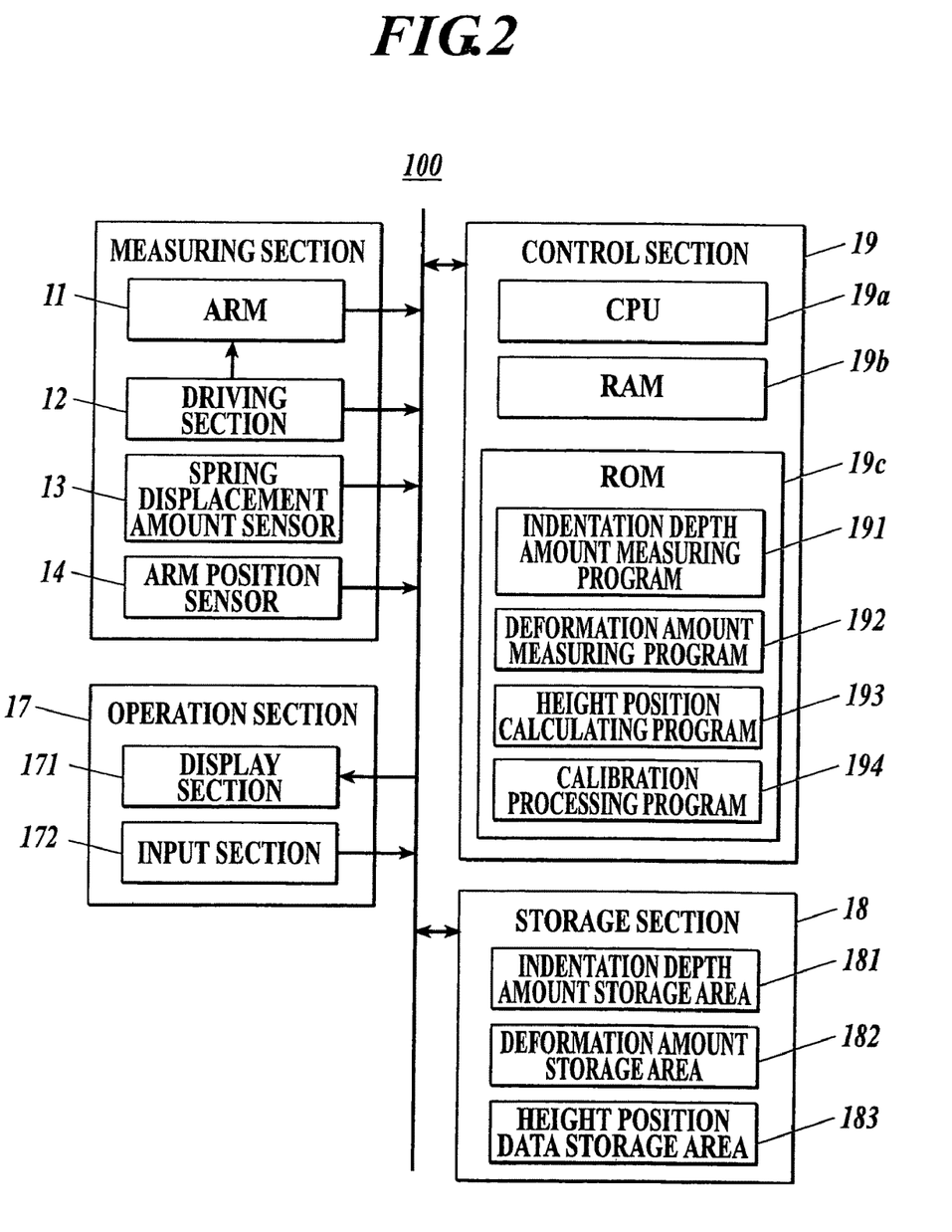
FIG. 2 is a block diagram showing a structure of a main section of the hardness testing instrument of the present embodiment.

As shown in FIG. 1 and FIG. 2, the hardness testing instrument 100 includes an arm 11 as a load applying section, driving section 12, spring displacement amount sensor 13, arm position sensor 14, specimen table 15, specimen table height adjustment section 16, operation section 17, storage section 18, control section 19 and the like.

The arm 11 is rotatably included in a testing instrument main body 100a and various indenters are replaceably mounted at a tip end.

As various indenters mounted to the arm 11 there are indenters such as indenter 1 for forming an indentation on a surface of a specimen, flat indenter (not shown) for pressuring without damaging a predetermined object, or the like.

The driving section 12 includes, for example, a piezoelectric element, force coil, etc., as a driving source 12a. Power generated by the driving source 12a is transmitted to the arm 11 through a leaf spring section 11a, and the arm 11 is rotated so that the tip end side of the arm 11 is close to the specimen table 15 to press the indenter 1 or flat indenter to the object (for example, specimen, reference block, load measuring instrument, etc.) placed on the specimen table 15.

The driving section 12 rotates the arm 11 in a direction away from the specimen table 15 and moves the arm 11 to a predetermined retracting position. The retracting position is a position where a distance is maintained between the various indenters and the specimen table 15 to exchange the indenter or the object on the specimen table 15 or to perform predetermined preparation for measurement.

The spring displacement amount sensor 13 detects a spring displacement amount of the leaf spring section 11a in the arm 11. Specifically, the spring displacement amount sensor 13 includes, for example, a displacement sensor unit (linear scale) to optically read a glass scale and can detect displacement amount of the leaf spring section 11a when the leaf spring section 11a transmits power generated from the driving source 12a of the driving section 12 to the arm 11. The displacement amount of the leaf spring section 11a detected by the spring displacement amount sensor 13 is output to the control section 19.

The arm position sensor 14 detects the moving amount of the arm 11. Specifically, the arm position sensor 14 includes, for example, a displacement sensor unit (linear scale) to optically read a glass scale and can detect the moving amount of the arm 11. The moving amount of the arm 11 detected by the arm position sensor 14 is output to the control section 19.

The specimen table 15 is provided below the various indenters mounted to the arm 11 and the object (for example, specimen, reference block, load measuring instrument, etc.) to which the various indenters are pressed are placed on the specimen table 15.

The specimen table height adjustment section 16 includes a strut section 16a with a male thread formed on an outer circumference face and a handle section 16b with a female thread formed on an inner circumference face, and the male thread of the strut section 16a and the female thread of the handle section 16b mesh together. The specimen table height adjustment section 16 functions as a specimen table height position adjustment section and by turning the handle section 16b, the strut section 16a can be moved in a vertical direction along a longitudinal direction of the strut section 16a and the specimen table 15 mounted on the top edge of the strut section 16a can be moved vertically to adjust the height position of the specimen table 15.

The operation section 17 includes, for example, a display section 171 including a liquid crystal panel and an input section 172 including a transparent touch panel provided on a display screen of the display section 171.

Various pieces of data and operation switches are displayed on the display section 171 of the operation section 17. By touch operation of the operation switch, etc. displayed on the display section 171, the input section 172 detects a position instructed by touching with position reading principles such as electromagnetic induction, magnetostriction, pressure-sensitivity, etc., and according to the detected position, input of various pieces of data, input of operation instruction, etc., can be performed. The input signal etc. instructed by touching on the operation section 17 is output to the control section 19.

Figure 3:
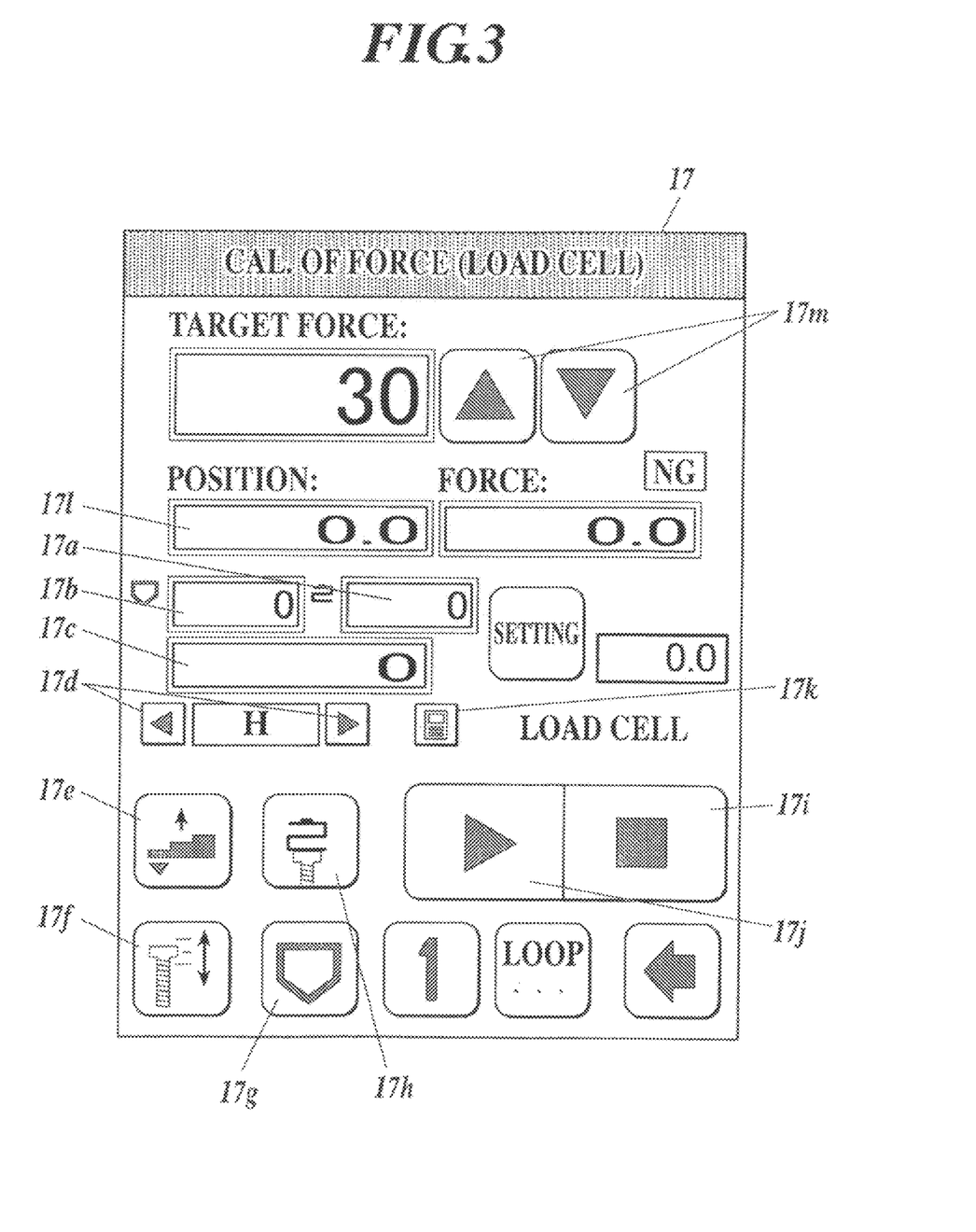
FIG. 3 is an explanatory diagram showing an example of an operation section.

As shown in FIG. 3, the operation section 17 includes a load cell distortion amount display frame 17a, indentation depth amount display frame 17b, specimen table height adjustment amount display frame 17c, calibration standard switching switch 17d, arm retracting switch 17e, specimen table height adjustment switch 17f, indentation depth amount measuring switch 17g, load cell distortion amount measuring switch 17h, force calibration start switch 17i, end switch 17j, indentation depth amount value input switch 17k, arm position display frame 17l, test force selection switch 17m and the like.

The storage section 18, for example, is a nonvolatile semiconductor memory, and includes an indentation depth amount storage area 181 which is an indentation depth amount storing section for storing an indentation depth amount measured by pressing with a predetermined load the indenter 1 to a reference block having a predetermined hardness on the hardness testing instrument 100 and a deformation amount storage area 182 which is a deformation amount storage section for storing a deformation amount of the load measuring instrument (for example, load cell) measured by pressing with a predetermined load the flat indenter to the load measuring instrument placed on the specimen table 15 on the hardness testing instrument 100.

The storage section 18 includes a height position data storage area 183 for storing height position data of the height position of the specimen table 15 according to hardness of the reference block obtained based on calculating difference between the deformation amount stored in the deformation amount storage area 182 and the indentation depth amount stored in the indentation depth amount storage area 181.

The control section 19 includes a CPU 19a, RAM 19b and ROM 19c, and controls the sections of the hardness testing instrument 100.

The CPU 19a reads out a processing program, etc., stored in the ROM 19c, expands the program to the RAM 19b and performs control of the entire hardness testing instrument 100.

The processing program, etc., performed by the CPU 19a is expanded to the program storage area in the RAM 19b and the input data, the processing result generated by performing the above-described processing program, and the like are stored in the data storage area.

The ROM 19c stores various pieces of data, various processing programs and the like to enable the CPU 19a to function to control the entire hardness testing instrument 100. Specifically, for example, as shown in FIG. 2, the ROM 19c stores an indentation depth amount measuring program 191, deformation amount measuring program 192, height position calculating program 193, calibration processing program 194, etc.

The indentation depth amount measuring program 191 is a program which allows the CPU 19a to realize a function of moving the arm 11 from the reference position, measuring the indentation depth amount when the indenter 1 is pressed with the predetermined load to the reference block having the predetermined hardness placed on the specimen table 15 and storing the indentation depth amount obtained by measuring in the indentation depth amount storage area 181 of the storage section 18.

In other words, by performing the indentation depth amount measuring program 191, the CPU 19a functions as a part of an indentation depth amount storage section to drive the driving section 12 to move the arm 11, to measure the indentation depth amount when an indentation is formed by pressing the indenter 1 with the predetermined load to the reference block having the predetermined hardness, and to store the indentation depth amount obtained by the measuring in the indentation depth amount storage area 181.

The CPU 19a as an indentation depth amount storage section measures the indentation depth amount when the indenter 1 is pressed with the predetermined load to a plurality of reference blocks having a different hardness placed on the specimen table 15 and stores the indentation depth of each of the plurality of the reference blocks in the indentation depth amount storage area 181. In other words, the indentation depth amount storage area 181 stores the plurality of indentation depth amounts according to the plurality of reference blocks having the different hardness.

The deformation amount measuring program 192 is a program which allows the CPU 19a to realize a function of moving the arm 11 from the reference position, measuring the deformation amount of the load measuring instrument when the flat indenter is pressed with the predetermined load to the load measuring instrument (load cell) placed on the specimen table 15, and storing the deformation amount obtained by measuring in the deformation amount storage area 182 of the storage section 18.

In other words, by performing the deformation amount measuring program 192, the CPU 19a functions as a part of a deformation amount storage section to drive the driving section 12 to move the arm 11, to measure the deformation amount of the load measuring instrument when the flat indenter is pressed with the predetermined load to the load measuring instrument, and to store the deformation amount obtained by the measuring in the deformation amount storage area 182.

The height position calculating program 193 is a program which allows the CPU 19a to realize the function of obtaining the height position of the specimen table 15 according to the hardness of the reference block based on calculating difference between the deformation amount stored in the deformation amount storage area 182 and the indentation depth amount stored in the indentation depth amount storage area 181.

In other words, by performing the height position calculating program 193, the CPU 19a functions as a height position obtaining section to calculate the difference between the deformation amount and the indentation depth amount to obtain height position data concerning the height position of the specimen table 15 for performing calibration with respect to each hardness of the reference block, and to store the height position data in the height position data storage area 183 of the storage section 18.

The calibration processing program 194 is a program which allows the CPU 19a to realize a function of performing calibration of a load by verifying whether or not the load measuring instrument (load cell) measures a predetermined load when the flat indenter is pressed with the predetermined load to the load measuring instrument placed on the specimen table 15 adjusted by the specimen table height adjustment section 16 to a height position obtained by the CPU 19a as a height position obtainment section.

In other words, by performing the calibration processing program 194, the CPU 19a functions as a calibration section to verify whether or not the load measuring instrument is measuring the predetermined load when the flat indenter is pressed with the predetermined load to the load measuring instrument placed on the specimen table 15 with the height position adjusted to perform the calibration with respect to each hardness of the reference block, and when it is verified the predetermined load is measured, to judge that the hardness testing instrument 100 has an accuracy of a certain load (test force).

Here, in order to perform calibration with respect to each hardness of the reference block, adjustment of the height position of the specimen table 15 is described.

Figure 4A:
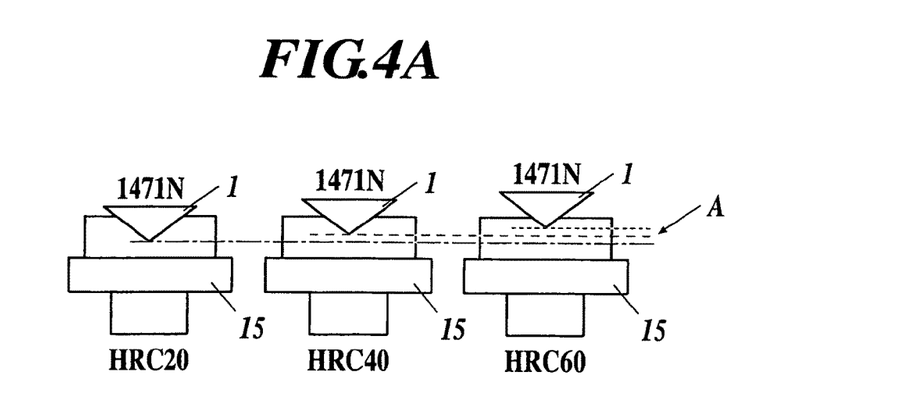
FIG. 4A is an explanatory diagram showing adjustment of height position of a specimen table in indentation amount measurement.

As shown in FIG. 4A, when the indenter 1 is pressed with a predetermined load by force of 1471 [N] to three reference blocks (HRC20, HRC40 and HRC60) having different hardness placed on the specimen table 15, each indentation depth amount is different and indentation is deeper in the soft HRC20 than the hard HRC60. The indentation depth amount measured by the hardness testing instrument 100 includes the machine casing distortion amount of the hardness testing instrument 100. In other words, (indentation depth amount; $h_f$)=(true indentation amount; A)+(machine casing distortion amount; D).

The CPU 19a as an indentation depth amount storage section measures the indentation depth amount ($h_f$) with respect to each of the plurality of (three) reference blocks and stores the amount in the indentation depth amount storage area 181.

Figure 4B:
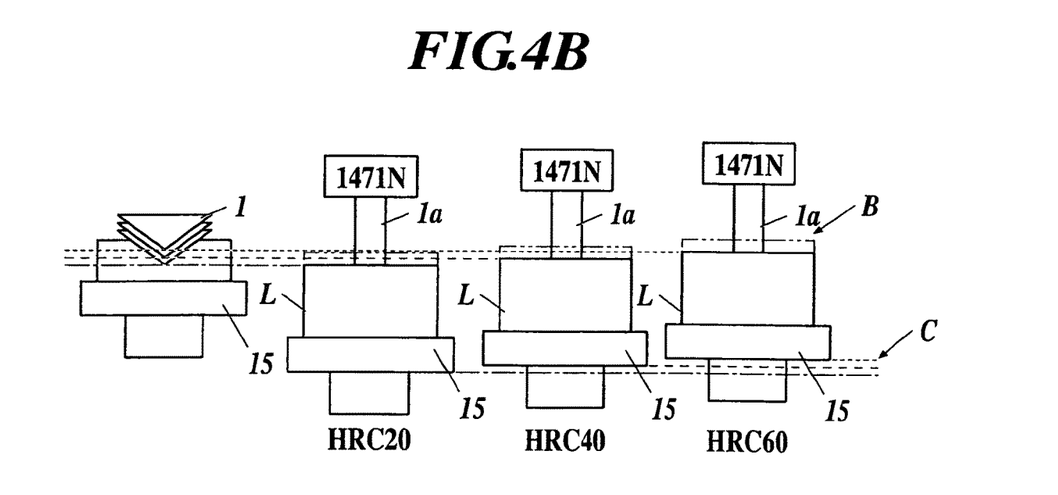
FIG. 4B is an explanatory diagram showing adjustment of height position of the specimen table in deformation amount measurement.

When the flat indenter 1a is pressed to the load cell L which is the load measuring instrument for measuring load in order to confirm whether or not the hardness testing instrument 100 outputs the predetermined load by force (load) of 1471 [N], since the load cell L is deformed by the force pressed by the flat indenter 1a, the deformation amount is measured similar to the indentation depth amount by the hardness testing instrument 100 to confirm the deformation amount of the load cell L. The deformation amount of the load cell L measured by the hardness testing instrument 100 includes the machine casing distortion amount of the hardness testing instrument 100. In other words, (indentation depth amount of the load cell; $h_L$)=(true deformation amount of the load cell; B)+(machine casing distortion amount; D).

The CPU 19a as a deformation amount storage section measures the deformation amount ($h_L$) of the load cell L and stores the amount in the deformation amount storage area 182.

Then, the height position of the specimen table 15 with respect to each hardness of the reference block is obtained so that the tip portion of the flat indenter 1a can be pushed against and press the load cell L at the position (height) corresponding to the tip portion of the indenter 1 with the reference block loaded with the predetermined load (1471 [N]) when calibration is performed according to the hardness of the reference block.

Difference (C) of the height position of the specimen table 15 with respect to each hardness of the reference block can be calculated by the following equation: (difference of height position of the specimen table; C)=($h_L$)−($h_I$)=(true load cell deformation amount; B)−(true indentation amount; A).

In other words, as shown in FIG. 4B, by pressing the flat indenter 1a to the load cell L placed on the specimen table 15 at the height position adjusted based on the difference (C) of the height position of the specimen table 15 obtained by calculating the difference between the deformation amount ($h_L$) of the load cell L and the indentation depth amount ($h_I$) according to the reference block, indentation of the flat indenter 1a to the load cell L can be performed at a height position corresponding to the tip portion of the indenter 1 with the reference block loaded with a predetermined load (1471 [N]) and the load can be measured at a suitable height position, therefore, calibration of the load according to the hardness of the reference block can be performed.

The calculated difference (C) of the height position of the specimen table does not include the machine casing distortion amount (D), therefore, calibration of load can be performed more accurately.

Figure 5:
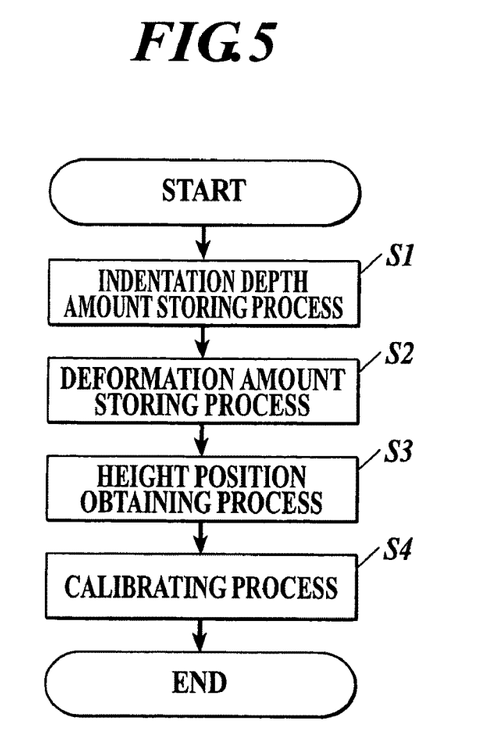
FIG. 5 is a flowchart showing main process steps of a calibration method of the hardness testing instrument of the present embodiment.

Next, a calibration method of the hardness testing instrument of the present invention is described based on a flowchart shown in FIG. 5.

Firstly, the indentation depth amount storing process will be described.

First, the test force selection switch 17m is operated to set the test force to be calibrated (step S101).

Next, the position of three standards where calibration is performed is determined (step S102). For example, the three standards are hard reference block (HRC60), intermediate hardness reference block (HRC40) and soft reference block (HRC20).

Next, the indenter 1 is mounted to an arm 11 of the hardness testing instrument 100 and the reference block is placed on the specimen table 15 (step S103).

Then, the force calibration start switch 17i is pushed (step S104).

Next, the handle section 16b is rotated to lift the specimen table 15 so that the indenter 1 and the reference block contact each other and adjustment is performed until the display in the arm position display frame 171 reads "0.0" which shows it is level (step S105).

Then, the arm retracting switch 17e is pushed to retract the arm 11 (step S106).

Next, the calibration standard switching switch 17d is operated to display a level of the set reference block in the display frame (step S107). The hardness level is changed by repeating L (soft)→M (intermediate)→H (hard).

Then, by pushing the indentation depth amount measuring switch 17g, the arm 11 is operated, indentation of the indenter 1 to the reference block is performed and the total test force is loaded to measure the indentation depth amount (step S108).

Then, after waiting five seconds (JIS total test force retention time) to avoid creep phenomenon, the arm retracting switch 17e is pushed to retract the arm 11 (step S109). At this time, the indentation depth amount ($h_1$) when the total test force is loaded is displayed in the arm position display frame 171 and this value ($h_1$) is stored in the storage section 18 and displayed in the indentation depth amount display frame 17b.

Then, the handle section 16b is operated to lower the specimen table 15, and by pushing the end switch 17j, the measuring of the indentation depth amount of the reference block ends (step S110).

From step S101 to step S110 are included in the indentation depth amount storing process (step S1).

These steps S101 to S110 are repeated for the three standards (HRC60, HRC40 and HRC20) and each indentation depth amount is measured and stored.

Secondly, the deformation amount storing process is described.

First, the flat indenter is mounted to the arm 11 of the hardness testing instrument 100 and the load cell is set on the specimen table 15 (step S201).

Then, the force calibration start switch 17i is pushed (step S202).

Next, the handle section 16b is rotated to lift the specimen table 15 so that the flat indenter and the load cell contact each other and adjustment is performed until the display of the arm position display frame 171 reads "0.0" which shows it is level (step S203).

Then, the arm retracting switch 17e is pushed to retract the arm 11 (step S204).

Next, by pushing the load cell distortion amount measuring switch 17h, the arm 11 is operated, indentation of the flat indenter to the load cell is performed and the total test force is loaded to measure the distortion amount (step S205).

Then, after waiting thirty seconds (procedure for use of force meter of JIS) to avoid creep phenomenon, the arm retracting switch 17e is pushed to retract the arm 11 (step S206). At this time, the load cell deformation amount ($h_1$) when the total test force is loaded is displayed in the arm position display frame 171 and this value ($h_1$) is stored in the storage section 18 and displayed in the load cell distortion amount display frame 17a.

From step S201 to step S206 are included in the distortion amount storing process (step S2).

Thirdly, the height position obtaining process is described.

First, the calibration standard switching switch 17d is operated to display the hardness level of the reference block to be calibrated in the display frame (step S301). The hardness level is changed by repeating L (soft)→M (intermediate)→H (hard).

Then, the height position of the specimen table 15 corresponding to the hardness level displayed in the display frame is calculated (difference of height position of specimen table (C)=($h_L$)−($h_I$)) and the value (C) of the obtained height position is displayed in the specimen table height adjustment amount display frame 17c (step S302). The value (C) is stored in the storage section 18.

Next, by pushing the specimen table height adjustment switch 17f, the arm 11 is moved and maintained at a position where the flat indenter applies to the load cell force small enough compared to the total test force (step S303).

Next, the handle section 16b is rotated and the height position of the specimen table 15 is adjusted so that the value displayed in the arm position display frame 17l becomes the value displayed in the specimen table height adjustment amount display frame 17c (step S304).

Then, the arm retracting switch 17e is pushed to retract the arm 11 (step S305).

From step S301 to step S305 are included in the height position obtaining process (step S3).

Fourthly, the calibrating process is described.

First, the force calibration start switch 17i is pushed and the arm 11 is moved to press the flat indenter to the load cell so that the total test power is loaded (step S401).

Then, after waiting thirty seconds (procedure for use of force meter of JIS) to avoid creep phenomenon, calibrating of the load is performed by comparing and verifying the value of the load measured by the load cell and the predetermined load value (1471 [N]) so as to verify whether or not the value of the measured load of the load cell is the predetermined load value (1471 [N]) (step S402). At this time, it can be seen that the value displayed in the arm position display frame 17l and the value displayed in the indentation depth amount display frame 17b are almost the same value. The values are not perfectly the same due to operation error when reference position is set, and allowance and hysteresis of the testing instrument.

Next, the arm retracting switch 17e is pushed to retract the arm 11 (step S403).

From step S401 to step S403 are included in the calibrating process (step S4).

These steps S401 to S403 are repeated for the three standards (HRC60, HRC40 and HRC20) and calibration with respect to each standard is performed.

As described above, according to the calibration method of the hardness testing instrument by the hardness testing instrument 100 of the present invention, the indenter 1 is pressed with the predetermined load to the plurality of reference blocks having different hardness placed on the specimen table 15 to measure the indentation depth amount to be stored, the flat indenter is pressed with the predetermined load to the load cell placed on the specimen table 15 to measure the deformation amount of the load cell to be stored and the difference between the deformation amount and the indentation depth amount is calculated to obtain the height position of the specimen table 15 in order to perform the calibration with respect to each hardness of the reference block.

By adjusting the specimen table 15 to the height position obtained by the calculation, calibration of the load in different standards according to the plurality of reference blocks having different hardness can be easily performed. In other words, by adjusting the specimen table 15 to the height position obtained by the calculation, the flat indenter can press the load cell at the height position corresponding to the tip portion of the indenter 1 when the reference block is loaded with a predetermined load and the load can be measured at a suitable height position, therefore, calibration of the load according to the hardness of the reference block can be done more easily and more accurately.

Particularly, since the arm 11 is comprised to be able to move to a retracting position away from the specimen table 15, data can be suitably obtained a plurality of times.

Calibration of preliminary test force can be performed by calibration of the three standards, similar to the calibration of the total test force described above, however it is preferable to perform with the process described below.

First, the test force selection switch 17m is operated and preliminary test force 10 kgf or 3 kgf is selected (step S501).

Next, the flat indenter is mounted to the arm 11 of the hardness testing instrument 100 and the load cell is set on the specimen table 15 (step S502).

Then, the force calibration start switch 17i is pushed (step S503).

Next, the handle section 16b is rotated to lift the specimen table 15 so that the flat indenter and the load cell contact each other and adjustment is performed until the display of the arm position display frame 17l reads "0.0" which shows it is level (step S504).

Then, the arm retracting switch 17e is pushed to retract the arm 11 (step S505).

Next, the force calibration start switch 17i is pushed to operate the arm 11 so that the flat indenter presses the load cell to load the preliminary test force (step S506).

Next, the handle section 16b is rotated and adjustment is performed until the display of the arm position display frame 17l reads "0.0" which shows it is level (step S507).

Then, the arm retracting switch 17e is pushed to retract the arm 11 (step S508).

Next, the force calibration start switch 17i is pushed to operate the arm 11 so that the flat indenter presses the load cell to load the preliminary test force (step S509).

Then, after waiting thirty seconds (procedure for use of force meter of JIS) to avoid creep phenomenon, calibrating of the preliminary test force is performed by verifying whether or not the value of the measured load of the load cell is the load according to the preliminary test force (step S510). At this time, it can be seen that the value displayed in the arm position display frame 17l and the value displayed in the indentation depth amount display frame 17b are almost the same value. The values are not perfectly the same due to operation error when reference position is set, and allowance and hysteresis of the testing instrument.

Next, the arm retracting switch 17e is pushed to retract the arm 11 (step S511).

In this way, the calibration of the preliminary test force can be performed.

The application of the present invention is not limited to the above-described embodiments, and can be suitably modified without leaving the scope of the spirit of the invention.

According to a first aspect of the preferred embodiments, there is provided a hardness testing instrument which measures a hardness of a specimen by pressing an indenter to a surface of the specimen, the hardness testing instrument comprising:

a load applying section with the indenter or a flat indenter mounted thereon;

a driving section to move the load applying section;

a specimen table on which an object to be pressed by the indenter or the flat indenter is placed;

a specimen table height adjustment section to adjust a height position of the specimen table;

an indentation depth amount storage section to move the load applying section from a reference position, to measure the indentation depth amount when the indenter is pressed with a predetermined load to a reference block having a predetermined hardness placed on the specimen table, and to store the indentation depth amount;

a deformation amount storage section to move the load applying section from the reference position, to measure the deformation amount of a load measuring instrument placed on the specimen table when the flat indenter is pressed with a predetermined load to the load measuring instrument, and to store the deformation amount;

a height position obtaining section to obtain a height position of the specimen table according to the hardness of the reference block based on calculating difference between the deformation amount stored in the deformation amount storage section and the indentation depth amount stored in the indentation depth amount storage section; and a calibration section to calibrate the load by comparing a value of the load measured by the load measuring instrument and a value of the predetermined load when the flat indenter is pressed with the predetermined load to the load measuring instrument placed on the specimen table adjusted by the specimen table height adjustment section to the height position of the specimen table obtained by the height position obtaining section.

Preferably, the hardness testing instrument further comprises a specimen table height position adjustment section to perform adjustment of a height of the specimen table so that the specimen table is at the height position obtained by the height position obtaining section when the flat indenter applies small enough force to the load measuring instrument placed on the specimen table, wherein the calibration section calibrates the load by comparing the value of the load measured by the load measuring instrument and the value of the predetermined load when the flat indenter is pressed with the predetermined load to the load measuring instrument placed on the specimen table adjusted by the specimen table height position adjustment section.

Preferably, in the hardness testing instrument, the indentation depth amount storage section measures each of the indentation depth amounts when the indenter is pressed with the predetermined load to a plurality of reference blocks having different hardness placed on the specimen table and stores the indentation depth amounts;

the height position obtainment section obtains a height position of the specimen table according to the hardness corresponding to the plurality of reference blocks based on calculating difference between the deformation amount stored in the deformation amount storage section and the indentation depth amount according to the hardness of the plurality of reference blocks stored in the indentation depth amount storage section; and the calibration section performs calibration with respect to each hardness of the plurality of reference blocks by verifying whether or not the load measuring instrument measures the predetermined load when the flat indenter is pressed with the predetermined load to the load measuring instrument placed on the specimen table adjusted to the height position of the specimen table according to the plurality of reference blocks.

Preferably, in the hardness testing instrument, the load applying section is comprised so as to be able to move to a retracting position away from the specimen table by the driving section.

According to a second aspect of the preferred embodiments, there is provided a calibration method for a hardness testing instrument to calibrate a hardness testing instrument comprising, a load applying section with the indenter or a flat indenter mounted thereon;

a driving section to move the load applying section;

a specimen table on which an object to be pressed by the indenter or the flat indenter is placed; and a specimen table height adjustment section to adjust a height position of the specimen table, the method comprising:

storing an indentation depth amount by placing the load applying section at a reference position by adjusting the height position of the specimen table so that the indenter is in contact with a plurality of reference blocks having different hardness placed on the specimen table, then moving the load applying section from the reference position to measure each indentation depth amount when the indenter is pressed with a predetermined load to each of the reference blocks, and storing the indentation depth amount in the storage section;

storing a deformation amount by placing the load applying section at a reference position by adjusting the height position of the specimen table so that the flat indenter is in contact with the load measuring instrument placed on the specimen table, then moving the load applying section from the reference position to measure the deformation amount of the load measuring instrument when the indenter is pressed with a predetermined load to the load measuring instrument, and storing the deformation amount in the storage section;

obtaining a height position of the specimen table according to the hardness corresponding to the plurality of reference blocks based on calculating difference between the deformation amount stored in the storage section and the indentation depth amount according to the hardness of the reference block stored in the storage section;

adjusting the specimen table height position by performing adjustment of the specimen table height to the height position of the specimen table obtained in the height position obtaining step when the flat indenter applies small enough force to the load measuring instrument placed on the specimen table; and calibrating the load by comparing a value of the load measured by the load measuring instrument and a value of the predetermined load when the flat indenter is pressed with the predetermined load to the load measuring instrument placed on the specimen table adjusted in the specimen table height position adjusting step.

According to these aspects, the indentation depth amount when the indenter is pressed with a predetermined load to the reference block placed on the specimen table of the hardness testing instrument is measured to be stored, the deformation amount of the load measuring instrument when the flat indenter is pressed with a predetermined load to the load measuring instrument placed on the specimen table of the hardness testing instrument is measured to be stored and the difference between the deformation amount and the indentation depth amount is calculated to obtain the height position of the specimen table according to hardness of the reference block.

By adjusting the specimen table to the height position obtained by the calculation, the flat indenter can be pressed to the load measuring instrument at the height position corresponding to the tip portion of the indenter when the reference block is loaded with a predetermined load and the load can be measured at a suitable height position, therefore, calibration of the load according to the hardness of the reference block can be done more easily.

The entire disclosure of Japanese Patent Application No. 2007-317404 filed on Dec. 7, 2007 including description, claims, drawings and abstract are incorporated herein by reference in its entirety.

Although various exemplary embodiments have been shown and described, the invention is not limited to the embodiments shown. Therefore, the scope of the invention is intended to be limited solely by the scope of the claims that follow.

What is claimed is:

1. A hardness testing instrument which measures a hardness of a specimen by pressing an indenter to a surface of the specimen, the hardness testing instrument comprising:
a load applying section with the indenter or a flat indenter mounted thereon;
a driving section to move the load applying section;
a specimen table on which an object to be pressed by the indenter or the flat indenter is placed;
a specimen table height adjustment section to adjust a height position of the specimen table; and
a computer processing unit to perform the functions of:
an indentation depth amount storage section configured to move the load applying section from a reference position, configured to measure an indentation depth amount when the indenter is pressed with a predetermined load to a reference block having a predetermined hardness placed on the specimen table, and configured to store the indentation depth amount in a storage area;
a deformation amount storage section configured to move the load applying section from the reference position, configured to measure a deformation amount of a load measuring instrument placed on the specimen table when the flat indenter is pressed with a predetermined load to the load measuring instrument, and configured to store the deformation amount in the storage area;
a height position obtaining section configured to obtain a height position of the specimen table according to the hardness of the reference block based on calculating a difference between the deformation amount stored in the storage area and the indentation depth amount stored in the storage area; and
a calibration section configured to calibrate the load by comparing a value of the load measured by the load measuring instrument and a value of the predetermined load when the flat indenter is pressed with the predetermined load to the load measuring instrument placed on the specimen table adjusted by the specimen table height adjustment section to the height position of the specimen table obtained by the height position obtaining section,
wherein the indentation depth amount storage section is configured to measure each of the indentation depth amounts when the indenter is pressed with the predetermined load to a plurality of reference blocks having different hardness placed on the specimen table and stores the indentation depth amounts in the storage area;
the height position obtaining section is configured to obtain a height position of the specimen table according to the hardness corresponding to the plurality of reference blocks based on calculating a difference between the deformation amount stored in the storage area and the indentation depth amount according to the hardness of the plurality of reference blocks stored in the storage area; and
the calibration section is configured to perform calibration with respect to each hardness of the plurality of reference blocks by verifying whether or not the load measuring instrument measures the predetermined load when the flat indenter is pressed with the predetermined load to the load measuring instrument placed on the specimen table adjusted to the height position of the specimen table according to the plurality of reference blocks.

2. The hardness testing instrument according to claim 1, wherein the specimen table height adjustment section is configured to perform adjustment of the height of the specimen table so that the specimen table is at the height position obtained by the height position obtaining section when the flat indenter applies small enough force to the load measuring instrument placed on the specimen table, and
the calibration section is configured to calibrate the load by comparing the value of the load measured by the load measuring instrument and the value of the predetermined load when the flat indenter is pressed with the predetermined load to the load measuring instrument placed on the specimen table adjusted by the specimen table height position adjustment section.

3. The hardness testing instrument according to claim 1, wherein the load applying section is configured to move to a retracting position away from the specimen table by the driving section.

4. A calibration method for a hardness testing instrument to calibrate a hardness testing instrument comprising, a load applying section with an indenter or a flat indenter mounted thereon; a driving section to move the load applying section; a specimen table on which an object to be pressed by the indenter or the flat indenter is placed; and a specimen table height adjustment section to adjust a height position of the specimen table, the method comprising:
obtaining an indentation depth amount by placing the load applying section at a reference position by adjusting the height position of the specimen table so that the indenter is in contact with a plurality of reference blocks having different hardness placed on the specimen table, then moving the load applying section from the reference position to measure each indentation depth amount when the indenter is pressed with a predetermined load to each of the reference blocks, and storing the indentation depth amount in a storage area;
obtaining a deformation amount by placing the load applying section at a reference position by adjusting the height position of the specimen table so that the flat indenter is in contact with the load measuring instrument placed on the specimen table, then moving the load applying section from the reference position to measure a deformation amount of the load measuring instrument when the indenter is pressed with a predetermined load to the load measuring instrument, and storing the deformation amount in the storage area;
obtaining a height position of the specimen table according to the hardness corresponding to the plurality of reference blocks based on calculating a difference between the deformation amount stored in the storage area and the indentation depth amount according to the hardness of the reference block stored in the storage area;
adjusting the specimen table height position by performing adjustment of the specimen table height to the height position of the specimen table obtained in the height position obtaining step when the flat indenter applies small enough force to the load measuring instrument placed on the specimen table; and
calibrating the load by comparing a value of the load measured by the load measuring instrument and a value of the predetermined load when the flat indenter is pressed with the predetermined load to the load measuring instrument placed on the specimen table adjusted in the specimen table height position adjusting step.

* * * * *